United States Patent [19]

Swerdloff

[11] Patent Number: 5,483,567
[45] Date of Patent: Jan. 9, 1996

[54] COMPUTERIZED METHOD FOR CONVERTING POLAR TOMOGRAPHIC DATA TO A CARTESIAN IMAGE FORMAT

[75] Inventor: Stuart J. Swerdloff, Madison, Wis.

[73] Assignee: Wisconsin Alumni Research Foundation, Madison, Wis.

[21] Appl. No.: 310,593

[22] Filed: Sep. 22, 1994

[51] Int. Cl.⁶ ............................ A61B 6/03; G01N 23/083
[52] U.S. Cl. ...................... 378/4; 378/901; 250/363.04; 128/653.4; 364/731; 364/413.16
[58] Field of Search ........................ 364/413.16, 413.17, 364/413.19, 731; 128/653.2; 290/363.04, 370.08, 370.09; 378/4, 901

[56] References Cited

U.S. PATENT DOCUMENTS

2,436,178  2/1948  Rajchman ............................ 364/731
4,208,721  6/1980  Eisenberg ............................ 364/731
5,333,164  7/1994  Tam .................................... 364/413.17

Primary Examiner—David P. Porta
Assistant Examiner—David Vernon Bruce
Attorney, Agent, or Firm—Quarles & Brady

[57] ABSTRACT

Tomographic data acquired in a polar reference frame is rapidly converted into data arranged in a Cartesian system suitable for processing and/or display by a program that may operate efficiently on an electronic computer. The program identifies each polar voxel, defining the region of the polar data, to one or more Cartesian voxels that overlap with it. Truncation techniques developed for use with computer graphics are used to determine an area of overlap between the voxels. Areas of overlap are indexed in a conversion table which may be used for rapid conversion between data acquired under these two coordinate systems.

14 Claims, 5 Drawing Sheets

COMPUTERIZED METHOD FOR CONVERTING POLAR TOMOGRAPHIC DATA TO A CARTESIAN IMAGE FORMAT

FIELD OF THE INVENTION

The present invention relates to medical imaging equipment such as MRI and CT systems in which data is acquired in a radially symmetric acquisition pattern and in particular to a method of formatting such data into a rectangular format for display and processing.

BACKGROUND OF THE INVENTION

Medical imaging systems such as computed tomography (CT) and magnetic resonance imaging (MRI) employ computer reconstruction techniques to convert acquired data into tomographic or "slice" images of a patient.

In CT, the acquired data consists of radiographic projections obtained with a fan beam of x-rays at regular angular intervals about the patient within the plane of the slice. A Fourier transformation of each projection provides a line of the Fourier transform of the desired slice image along a line of diameter about the center of rotation of the projections. A set of projections at different angles, therefore, provides a set of different lines of Fourier data arranged like spokes in a wheel. This Fourier data is converted to a rectangular or Cartesian format and the two-dimensional inverse Fourier transform is taken to produce the tomographic image.

In MRI, the acquired data is a sampled nuclear magnetic resonant (NMR) signal received from the patient after stimulation by a radio frequency (RF) electromagnetic field and during the application of one or more magnetic gradient fields. The gradient fields are produced by amplifiers driving conductive coils so the gradient fields may be varied in a "sequence" during the imaging. Multiple NMR signal acquired during the sequence, produce a field of data within a Fourier "k-space". This field of data is operated on by the two dimensional Fourier transform to produce the tomographic image. In one gradient sequence that reduces the peak power required of the gradient amplifiers, each acquisition of an NMR signal produces data along a spiral path through the k-space. As with CT, it is typical to convert this data to a Cartesian format to process and display it.

In both CT and MRI, each acquired data point is associated with an elemental measurement volume (voxel), either in the patient or in the Fourier space of the transformed data. As a result of the radial nature of the acquisition, the voxels are sectors of cylindrical annuluses arranged about a common center within a slice plane, their exact dimensions being determined by the resolution of the system. Normally, the thickness of the voxels (measured normal to the image plane) is constant and thin so that the voxels may be treated practically as areas rather than volumes. Voxels of this type will be termed "polar voxels" and the associated delta will be termed "polar data".

As noted above, accurate and efficient processing of a tomographic image requires that the polar data be converted to data values associated with rectangular voxels arranged in lines. These voxels will be termed "Cartesian voxels" and their associated data will be termed "Cartesian data". Cartesian data is easier to process and most commercial display devices, such as CRTs, enforce the use of data in a Cartesian format as a result of their scanning pattern.

Ideally, the conversion between polar data and Cartesian data accurately reflects the relative size, shape, orientation and position of the associated polar voxels and Cartesian voxels. Thus, a simple interpolation between polar data and closest Cartesian data based on the centers of the voxels is unacceptable.

Accurate conversion reflecting the relative size, shape, orientation and position of the associated polar voxel and Cartesian voxel can be difficult. There is no simple relationship between the position and relative orientation of polar voxels and Cartesian voxels. This is compounded by the fact that the shape and area of the polar voxels will generally change depending on their distance from the center of the polar reference frame.

The intractability of this conversion process has led to the development of an oversampling technique where the polar voxels are superimposed on an extremely fine Cartesian grid and each of the Cartesian voxels is cataloged as being inside or outside a given polar voxel. After a large number of such points are cataloged, the number of Cartesian voxels in each polar voxel is used to establish a conversion weight. Although this technique can provide an arbitrarily high degree of accuracy, it is extremely inefficient and time consuming.

A table incorporating the conversion weights may be used for multiple conversions provided the relative size, number and positioning of the polar and Cartesian voxels is not changed. Any change in the relative size, number or positioning of the polar and rectangular coordinates, however, requires a completely new calculation of this table. There is no simple operation on the conversion weights that will produce a new table for such changes in the structure of the rectangular or polar voxels. Thus the need for a computationally efficient means for converting polar data to Cartesian data or generating a conversion table is needed.

SUMMARY OF THE INVENTION

The present invention provides an extremely accurate and computationally efficient method of converting tomographic data, in a polar format, into Cartesian data suitable for subsequent reconstruction or display. The process makes use of truncation techniques developed for the computer graphics industry together with a compact description of each polar voxel to rapidly compile a list of weights for the conversion of polar data into Cartesian data.

Specifically, the present invention provides a tomographic imaging system having a detector providing a plurality of polar values related to physical characteristics of an imaged object, the polar values associated with corresponding polar volume elements arranged in concentric rings. An electronic computer receives these polar values from the detector and executes a stored program to identify the Cartesian volume elements overlapping a given current polar volume element in a predetermined mapping of polar volume elements to Cartesian volume elements.

For a current overlapping Cartesian volume element, the current polar volume element is truncated as if displayed in a window equal in size to the current overlapping Cartesian volume element to produce a truncated polar volume element. The area of the truncated polar volume element is calculated to produce a weight value which is identified to both the current overlapping Cartesian volume element and the current polar volume element. This step is repeated for all of the identified overlapping Cartesian elements and then the entire process is repeated for each of the polar volume elements. Cartesian values associated with the Cartesian volume elements are determined by summing, over all weight values associated with a Cartesian volume element, the product of the weight value times the polar data of the polar volume element identified with the weight value.

Thus, it is one object of the invention to provide a rapid computational method suitable for use on an electronic computer that may convert data taken in a polar coordinate system to a Cartesian format while accurately taking into account the size and shape, orientation and relative positions of the various voxels. By formulating the conversion process as one of truncating the polar voxels against the regular, rectangular Cartesian voxels, the conversion is made simple and fast. The polar values may be Fourier transformed x-ray attenuation data or sampled nuclear magnetic resonance signals acquired by a magnetic resonance imaging system, or other similar tomographic data.

The origin defining the polar volume elements and the origin of the axes defining the Cartesian volume elements may be the same and the boundaries between polar volume elements may lie along the Cartesian axes.

Thus it is another object of the invention to permit the rapid identification of overlapping Cartesian voxels for a given polar voxel by insuring that the origins and axes are aligned so only the vertices of the polar voxel need be examined to determine the overlapping Cartesian coordinates.

The production of a truncated polar volume element may be performed by evaluating a series of segments defining the current polar volume element and calculating intersections between those segments and similar segments defining the identified Cartesian volume element to create a new series of segments defining the truncated polar volume element.

Thus it is another object of the invention to provide a computationally efficient method of determining relative overlap between two voxels of arbitrary size, shape, orientation, and position.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference must be made therefore to the claims herein for interpreting the scope of the invention.

DETAILED DESCRIPTION OF THE PREFERRED EMBODIMENT

Imaging Hardware

Figure 1:
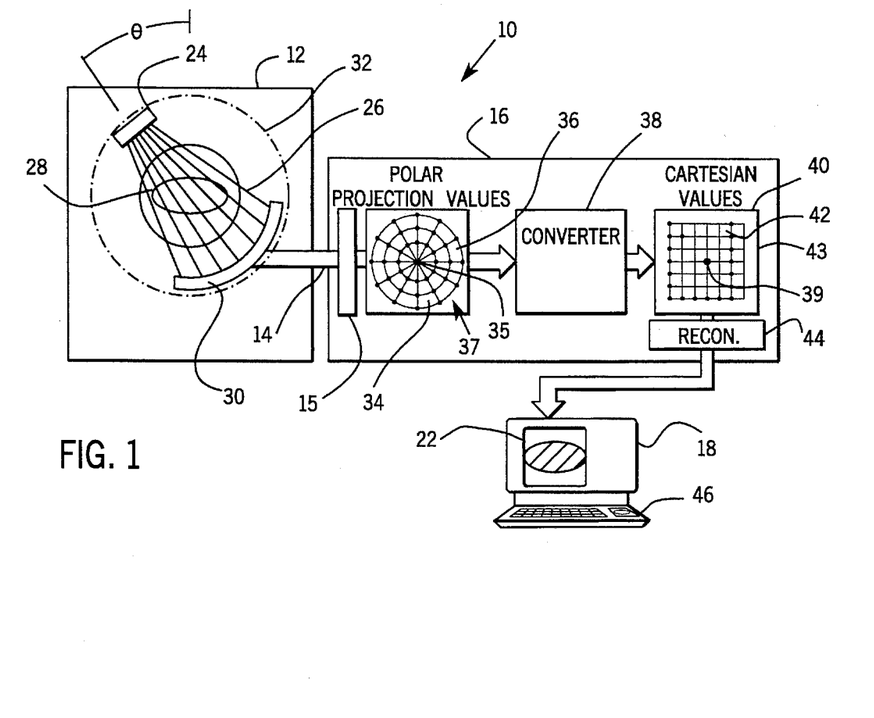
FIG. 1 is a schematic block diagram of a CT machine showing a fan beam CT scanner producing polar projection values received a reconstruction computer which produces Cartesian values for reconstruction and display on a display terminal.

Referring to FIG. 1, a CT machine 10, suitable for use with the present invention and as is generally known in the art, includes a gantry unit 12 communicating with a reconstruction computer 16. The reconstruction computer 16 is a general high speed Von Neumann type electronic computer but may include an array processor for the necessary reconstruction computations. A display console 18 receives data from the reconstruction computer 16 to produce a tomographic image 22. General parameters relating to the acquisition of the tomographic image 22 may be entered by means of a keyboard 46 associated with the display console 18 and communicating with the reconstruction computer 16.

The gantry unit 12 provides an x-ray source 24 producing a fan beam 26 passing generally along a transverse plane through a patient 28 to be received by a detector 30. The x-ray source 24 and detector 30 are mounted on a rotating gantry 32 so that an angle θ of the fan beam 26 as it passes through the patient 28 may be varied. The attenuation of the fan beam 26 as measured by the detector 30 at a given angle θ provides a "projection". Projection data 14 is transmitted to the reconstruction computer 16.

Overview of the Imaging Process

As a first step in the production of the tomographic image 22, projections are taken for different angles θ (generally over 360°) to form a "projection set". A preprocessing routine 15 takes the Fourier transform of the projection data 14 to produce a set of polar values 34 stored in the reconstruction computer 16 as an array 37. In the array 37 each polar value 34 is associated with a polar volume element (voxel) 36 representing a portion of the Fourier space of the polar values 34.

Each polar voxel 36 is identified to polar coordinates r and θ where θ generally equals the angle of the gantry 32 at which the polar value 34 was acquired and can be thought of as an angle about a center or origin 35 of the Fourier space of the polar voxels 36. The coordinate r is a spatial frequency measured by the polar value 34 and can be thought of as a distance from the origin 35 to the polar voxel 36.

The circumferential extent of each polar voxel 36 is determined by the number of different projections taken over 360° of gantry rotation whereas the radial extent of each voxel is determined generally by the number of individual detector elements in the detector 30 and thus the spatial resolution of the detector 30 and accordingly, the frequency resolution of the sampled Fourier transform of the projection data 14.

The reconstruction of the Fourier polar values 34 into the tomographic image 22 is most easily done in a Cartesian reference frame. Therefore the polar values 34 are next converted to Cartesian values 43 by means of a converter routine 38 in reconstruction computer 16. The converter routine 38 will be described in detail below.

Like the polar values 34, each resulting Cartesian value 43 is stored in an array 40 in the reconstruction computer 16 and associated with a Cartesian voxel 42. Cartesian voxels 42 are defined by coordinates x and y representing distances of the Cartesian voxels 42 from an origin 39 along perpendicular axes in the Fourier space. Generally, the height and width of each Cartesian voxel 42 is uniform and dependent on the desired display resolution of the tomographic image 22 and the resolution of the projection data 14.

Once the polar values 34 are converted into Cartesian values 43, the Cartesian values 43 are reconstructed into a tomographic image 22 by reconstruction routine 44 implemented in software in the reconstruction computer 16. The reconstruction routine 44 takes the two-dimensional Fourier transform of the Cartesian values 43 along the x and y axes.

Polar to Cartesian Conversion

A. Generating a Segment List

Figure 2:
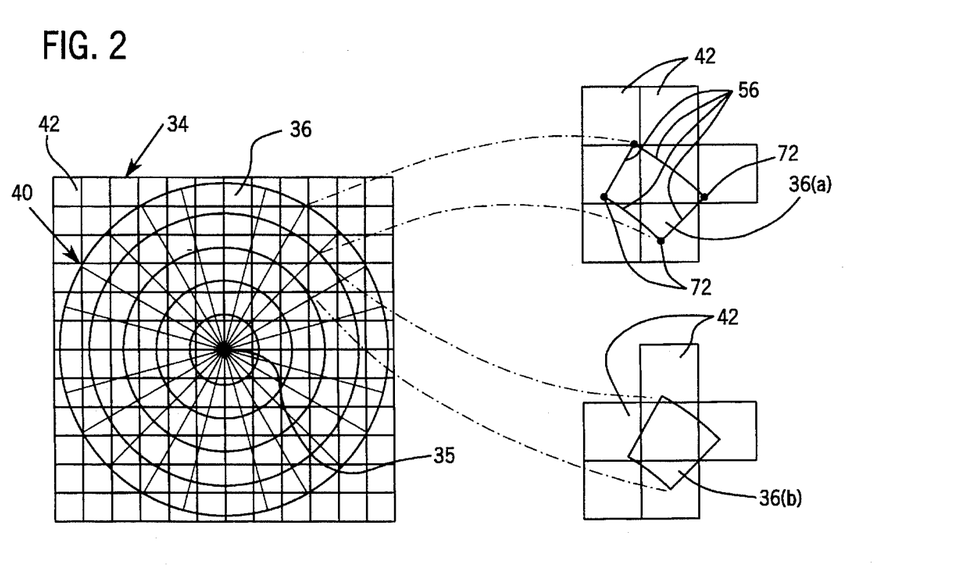
FIG. 2 is a simplified diagrammatic representation of overlapping polar and Cartesian voxels oriented so as to have coincident origins and so that polar voxels are separated along the Cartesian axes and showing the complex relationship between polar and Cartesian voxels for two polar voxels.
Figure 3:
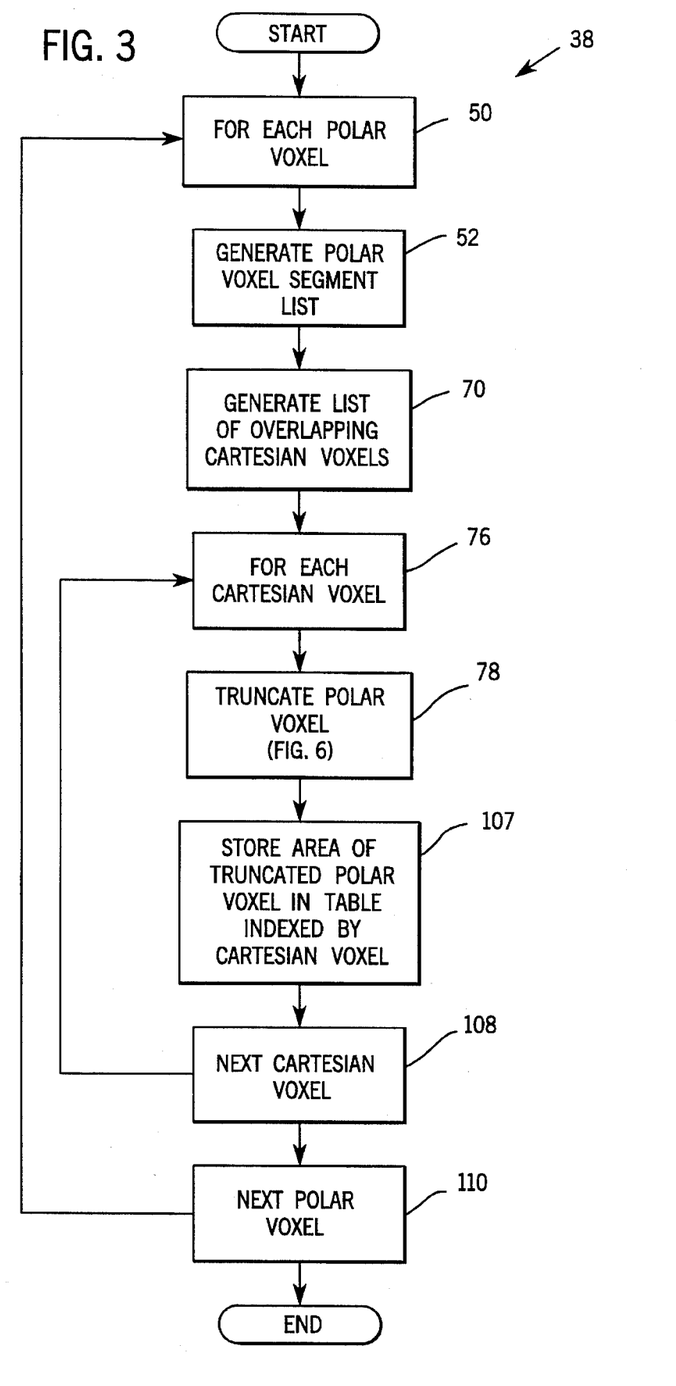
FIG. 3 is a flow chart of a program executed by the computer of FIG. 1 showing the steps of generating a conversion table for converting between polar data and Cartesian data through the use of repeated truncation of the polar voxels.
Figure 4:
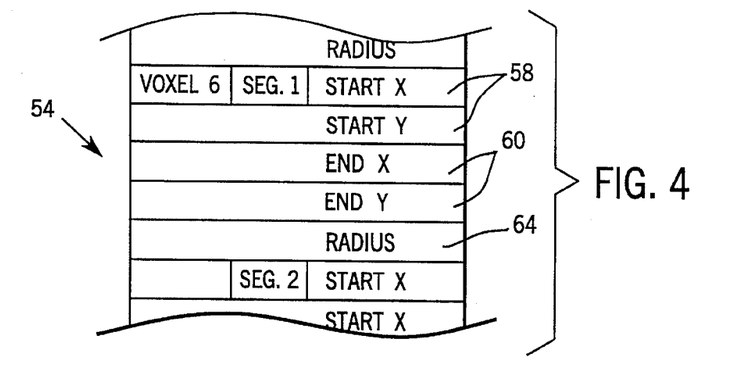
FIG. 4 is a schematic representation of a given polar voxel in computer memory.

Referring now to FIGS. 2, 3, and 4, different polar voxels 36a and 36b will in general have different sizes, shapes, orientations and positions. Accordingly, the process of converting the polar values 34 to Cartesian values 42 by converter program 38 starts, as represented by process blocks 50 and 52, (FIG. 3) by describing each of the polar voxels 36 by means of a segment list 54 stored in the memory of the reconstruction computer 16. The segment list 54 relates a unique index value associated with each voxel 36 to a list of its segment 56.

The index value ranges from one to the number of voxels 36. In the simplest case, where the voxels 36 all subtend equal angles and are all aligned along sectors of a circle, the index value may start at the inner most ring of voxels near the origin 35 and proceed clockwise around a ring, and upon completion of the ring, proceed to the next outer ring in like fashion.

The segments 56 associated with each index value describes the perimeter of the voxel 36 by means of its vertices 72 (in Cartesian coordinates) and the arcs of its segments 56. Each polar voxel 36 is considered to have four segments 56 with the innermost voxels 36 having one segment of zero length. Thus, the amount of memory space occupied by each voxel 36 in the segment list 54 is the same, permitting ready identification of those memory elements holding information for any given segment 56 of any given voxel 36.

For each voxel 36, two opposed segments 56 are straight and two opposed segments 56 are arcs of different radii but a common center of the origin 35. The segment list 54 thus stores for each index value, and for each of four segments 56, a starting segment vertex 58 defined by a starting x and y Cartesian coordinate, and an ending segment vertex 60 also defined by a Cartesian coordinate x and y. If the segment is an arc, a radius value 64 indicates the radius of that segment otherwise radius value contains a zero interpreted as indicating that the segment is a straight line.

B. Identifying Overlapping Cartesian Voxels

Referring again to FIG. 3, at process block 70 immediately following the generation of the segment list 54 for a given polar voxel 36, all Cartesian voxels 42 overlapping the given polar voxel as selected at process block 50 are identified. Each Cartesian voxel 42 is also given a unique index value. For example, starting in the upper left hand corner, the voxels may be numbered from left to right in rows continuing from top row to bottom row. Unlike the polar voxels 36, the size and orientation of the Cartesian voxels 42 is uniform and a segment list is not required. Instead, an explicit algebraic definition of the Cartesian coordinates of the vertices of the voxels 42 based on the index number may be readily determined by those of ordinary skill in the art.

Figure 5:
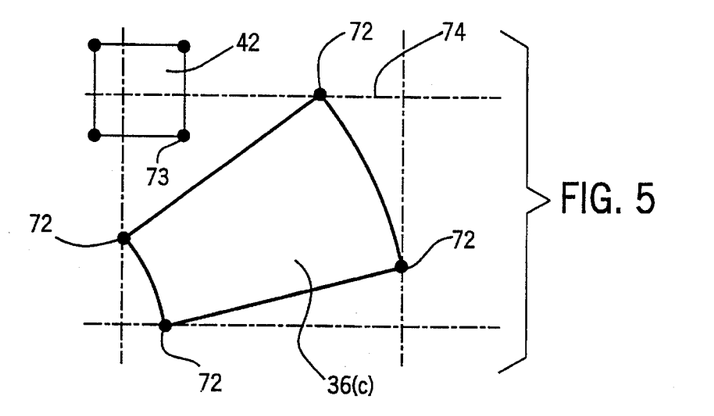
FIG. 5 is a schematic representation of a polar voxel showing the determination of overlapping Cartesian voxels from the vertices of the polar voxel.

Referring then to FIGS. 3 and 5, the identification of the overlapping Cartesian voxels 42 for a given polar voxel 36c may be performed examining each of the vertices 72 of the polar voxel 36 to define an inclusion rectangle 74 circumscribing the polar voxel 36. Each side of the inclusion rectangle intercepts one vertice 72 and is parallel to one of the x- or y-axes. This inclusion rectangle 74 may be generated simply by examining the x and y coordinates of the starting and ending points of 58 and 60 of each segment and selecting those coordinate values furthest from the center of mass of the vertices 72. The inclusion rectangle will thus be defined by two y-axis values and two x-axis values. Overlapping Cartesian voxels 42 may identified simply as those having one or more vertices 73 within the inclusion rectangle. This determination involves only two simple comparison operations to the each of the vertices x and y coordinates and is extremely rapid on a computer.

This procedure will, in certain cases, identify Cartesian voxels 42 in the neighborhood of the polar voxel 36 that are not in fact overlapping with the area of the polar voxel 36. As will be seen, this is not a problem because those voxels 42 will ultimately be given zero weight in the conversion process. Alternatively, the Cartesian voxels 42 identified by the inclusion rectangle 74 may subsequently be evaluated against the actual area of the polar voxel 36 to see if the vertices are in fact within that polar voxel 36 as defined by the segment list 54.

In the preferred embodiment, the selection of the number and size of the polar voxels 36 is constrained so that boundaries between polar voxels 36 align with the Cartesian axes of the Cartesian voxels 42. This means that the entire area of the polar voxel 36 will in fact lie within the inclusion rectangle 74. Generally, however, this restriction need not be enforced if the intersections between the segments of the Cartesian voxels and segments of the polar voxels are compared directly, accepting the corresponding penalty in computational time.

C. Truncation of the Polar Voxels

Once the list of overlapping Cartesian voxels has been generated at process block 70, then at process block 76, each of those identified overlapping Cartesian voxels 42 is used as a window against which to truncate the polar voxel 36 per process block 78. This truncation process evaluates what portion of the area of the polar voxel 36 overlaps the area of the Cartesian voxel 42.

Figure 6:
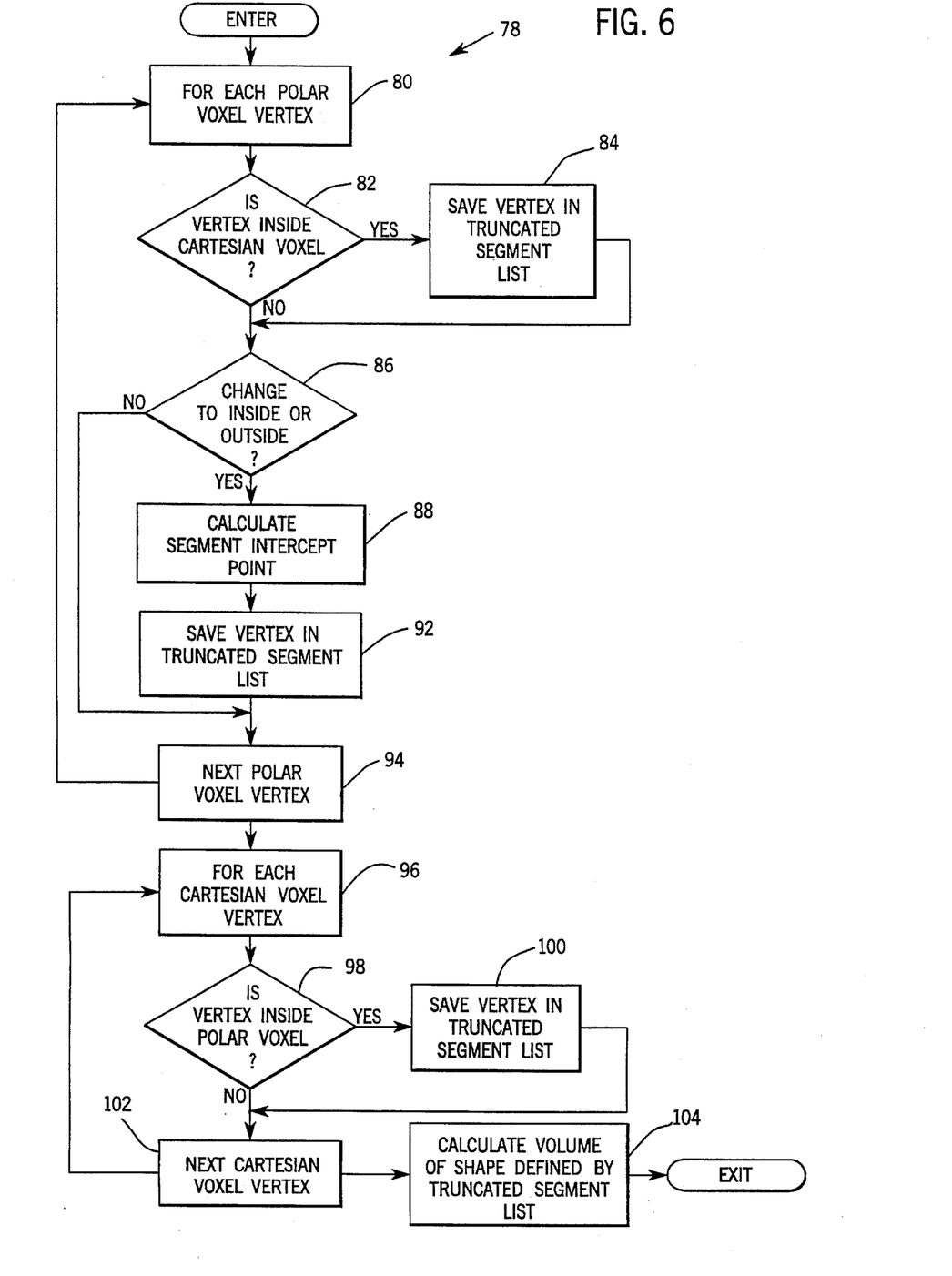
FIG. 6 is a flow chart of the truncation operation of FIG. 3 for determining a truncated polar voxel for each overlapping Cartesian voxel.
Figure 7:
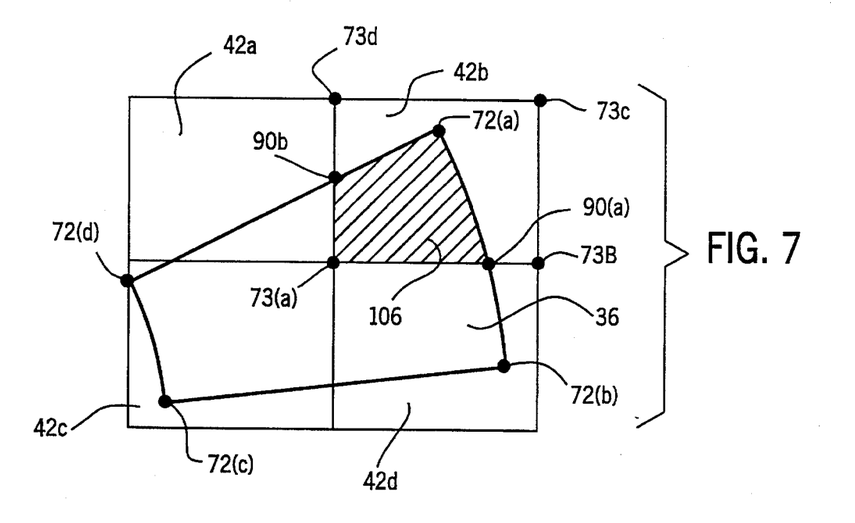
FIG. 7 is a view of the voxel of FIG. 5 and its overlapping Cartesian voxels showing the truncation process of FIG. 6.

Referring now to FIGS. 6 and 7, the truncation process of process block 78 first considers each vertex 72a through 72d of the polar voxel 36, as stored in the segment list 54, and as indicated at process block 80. At decision block 82, a determination is made as to whether the particular vertex 72 is inside or outside of a Cartesian voxel 42. Like the determination of whether vertices of the Cartesian voxels are inside of the inclusion rectangle 74, this determination requires only four rapid comparison operations.

For example, as shown in FIG. 7, a first vertex 72a of the polar voxel 36 is inside the Cartesian voxel 42b. In this case, at decision block 86, the routine 78 proceeds to process block 84 and that vertex 72a is saved in a truncated segment list (not shown) in the memory of the reconstruction computer 16. Initially, for each evaluated overlapping Cartesian voxel 42 considered by the truncation routine 78, the truncated segment list is cleared so that vertex 72a is the first vertex of the truncated segment list. Each vertex saved in the truncated segment list is designated by an x and y coordinate.

After a vertex has been saved in the truncated segment list per process block 84 or if the vertex is not within the Cartesian voxel being examined, the routine 78 proceeds to decision block 86 where it is determined whether there has been a transition from outside the Cartesian voxel 42b to inside the Cartesian voxel 42b or in the other direction from inside the Cartesian voxel 42b to outside the Cartesian voxel 42b.

In the example of vertex 72a, this vertex is the first vertex to be considered in the routine 78 and thus no transition has occurred. Accordingly, the routine 78 branches back to process block 80 and the next vertex of the polar voxel 36 from the segment list 54 is considered. That next vertex is 72b. In this example, vertex 72b is outside of the current Cartesian voxel 42b and therefore the routine 78 proceeds from process block 80 through decision block 82 directly to decision block 86. At decision block 86, there has been a change from a vertex inside the Cartesian voxels 42b to a vertex outside the Cartesian voxels 42b. Accordingly, the routine 78 branches to process block 88.

At process block 88 an intercept point 90 is calculated on the segment which crosses the perimeter of the current overlapping Cartesian voxel 42. This calculation of the intercept point 90 is a well understood exercise in trigonometry and requires the determination of the segment characteristics as an arc or straight line and if an arc determination of what its radius is from the segment list 54. Once the intercept point 90 has been calculated, the intercept point 90 is saved in the truncated segment list for process block 92 together with the radius of curvature 64 of the segment between point 72a and intercept point 90.

After the intercept point 90 is saved, or if there is no intercept point 90 because the previous and current vertices 72 were both inside or both outside of the Cartesian voxel 42, the routine 78 proceeds to process block 94 and the next polar voxel vertex 72 is examined by branching back to process block 80.

If at process block 94, all the polar voxel vertices 72 have been examined, and saved in the truncated segment list if they are inside the Cartesian voxel 42, and the appropriate intercept points 90 have also been saved, then the routine 78 proceeds to process block 96 and each of the Cartesian voxel vertices 73a–73b are examined in sequence. At decision block 98, it is determined whether these vertices 73 are inside or outside of the polar voxel 36. If they are inside the polar voxel 36 as, for example, vertex Θa of FIG. 7, this vertex 73a is also saved in the truncated segment list at process block 100. In either case, the routine 78 proceeds to process block 102 where the next Cartesian voxel vertex 73 is selected and the routine 78 branches back to process block 96 and that vertex 73 is examined to see if it is within the polar voxel 36.

D. Generating a Connection Table

Once all the Cartesian voxel vertices 73 have been examined per process blocks 96 and 102, the routine 78 proceeds to process block 104 where the area 106, defined by the vertices 72 and 73, and the intercept points 90 saved in the truncated segment list, is calculated. This calculation requires reference to the segment list 54 to determine which segments 56 of the truncated polar voxel 36 are arcs and the radius of those segments 56 and is performed by subdividing the area 106 into triangles, sectors of a circle and trapezoids, each of which may have its area determined by well known mensuration formulae.

Referring now again to FIG. 3, this area of the truncated polar voxel (defined in the present example by vertex 72a, 90a, 73a and 90b) is stored in a conversion table 105 indexed by the index number of the Cartesian voxel to which it is associated and indicating the index number of the polar voxel 36 of which it is a part.

Figure 8:
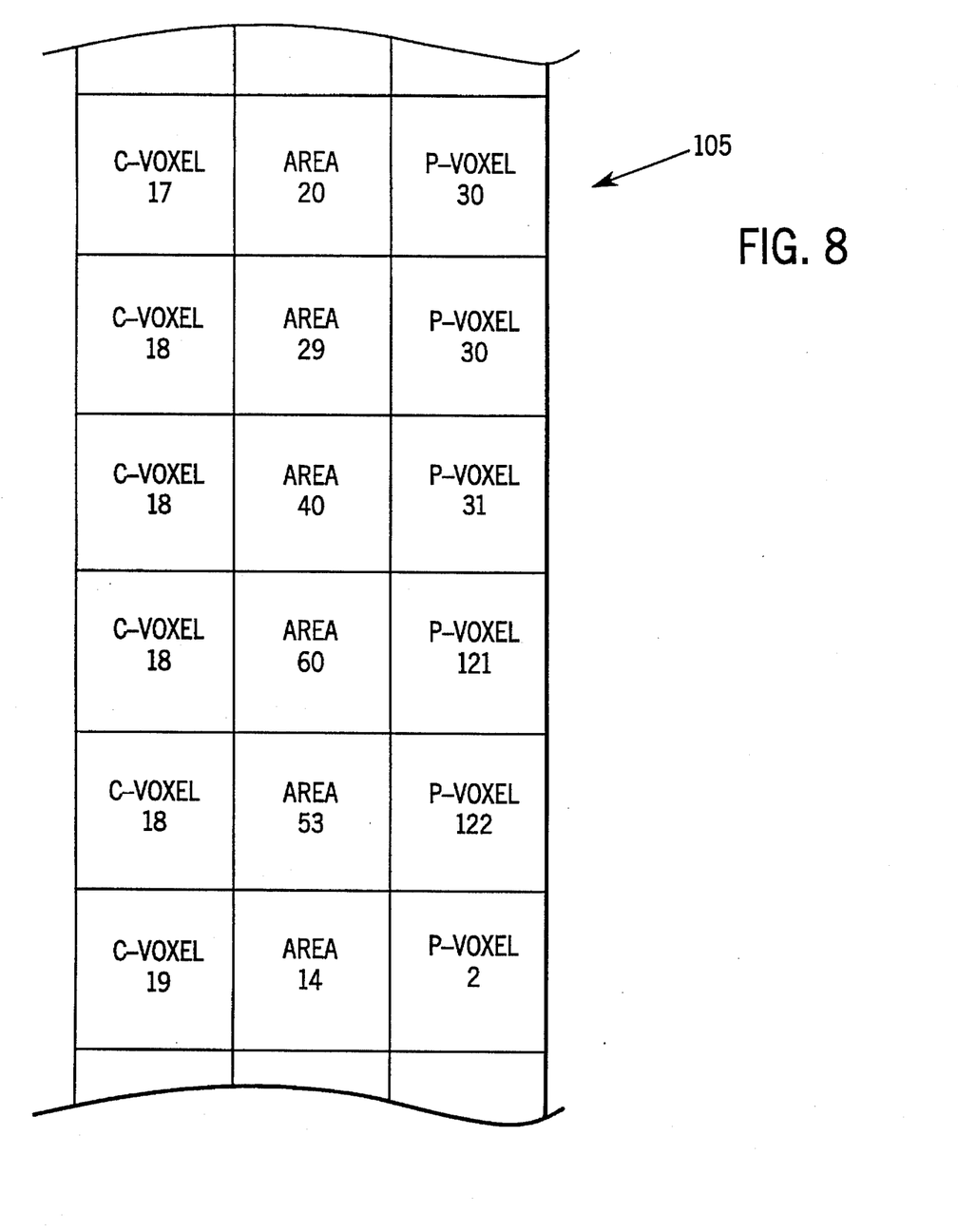
FIG. 8 is a schematic representation of the conversion table between polar data and Cartesian data as stored in computer memory.

Referring now to FIG. 8, this conversion table 105 may be stored in the reconstruction computer 16 as a linked list, a technique well understood to provide for the efficient storage of related elements. For clarity of description, however, the conversion table will be represented herein as a matrix having three columns, a first column identifying the index value of the Cartesian voxel 42, a second column indicating the area 106 of the polar voxel 36 overlapping the Cartesian voxel 42 of the first column and a third column representing the index value of the overlapping polar voxel 36. The matrix may be sorted by Cartesian voxel index number to permit them to be looked-up rapidly. Note that in the alternative, the matrix may be sorted by polar voxel index number to allow Cartesians to polar conversion.

This conversion table 105 has an arbitrary number of rows depending on the particular combinations of overlapping between Cartesian and polar voxels and on the number of Cartesian and polar voxels.

When the area 106 has been stored, per process block 107, the next Cartesian voxel 42 that overlaps the particular polar voxel 36, for example, Cartesian voxel 42a in FIG. 7, is examined and the converter program 38 returns to process block 76 to provide a new truncation of the polar voxel 36.

Once each overlapping Cartesian voxel has been identified and examined per process blocks 108 and 76 and the process blocks therebetween, the converter program 38 proceeds to process block 110 and the next polar voxel 36 is examined by looping back to process block 50.

At the conclusion of the program, each polar voxel 36 will have been examined and its areas of overlap 106 with Cartesian voxels 42 will have been identified to the particular Cartesian voxels per the conversion table 105.

E. Determining Cartesian Values from the Conversion Table and the Polar Values

The conversion table 105 may now be used to convert data in a polar format as acquired in MRI and CT machines to the Cartesian format necessary for conventional CRT type displays. This conversion process provides a Cartesian value of each Cartesian voxel 42 by looking up the index value of the Cartesian voxel 42 in the conversion table 105 and summing together contributions from each row of the conversion table 105 identified to that Cartesian voxel. The contribution from each row is the polar value of the polar voxel 36 identified by that row times the area 106 of overlap previously calculated and given in the second column of the conversion table 105. Note that the areas should sum to a constant value because unlike the polar voxels, each Cartesian voxel is of identical area. This fact may be used to evaluate the accuracy of the conversion process, variations in area represent errors in the conversion table 105.

Thus, for example, as shown in FIG. 8, the value associated with Cartesian voxel 42 having index number "18" would be equal to the polar value associated with polar voxel 36 with index number "30" times the area 106 (having a depicted value of "29") plus the polar value associated with polar voxel 36 with index number "31" times its depicted area 106 of "40", plus the polar value associated with polar voxel 36 having index number "121" times its depicted area 106 of "60" plus the value associated with polar voxel 36 having index number "122" times the area 106 depicted as "53".

Thus, the present invention provides an extremely rapid way of generating a conversion table 105 which can be saved and used for repeated numbers of conversions provided the relative size and orientations of the polar and Cartesian voxels do not change.

It will be understood that the conversion table 105 may also be generated on a separate freestanding computer other than the reconstruction computer 16 with the conversion table 105 simply loaded into the reconstruction computer 16 to provide the necessary conversions as long as the dimension and number of Cartesian voxels relative to the polar voxels does not change.

As noted before, even a minor change in the relationship or size and number of the polar voxels relative to the Cartesian voxels requires a wholly new calculation of the conversion table 105 as there is no simple transformation of the values of the conversion table 105 based on changes in these relative size, shape, number and orientation of the Cartesian and polar coordinates.

The above description has been that of a preferred embodiment of the present invention. It will occur to those that practice the art that many modifications may be made without departing from the spirit and scope of the invention. In order to apprise the public of the various embodiments that may fall within the scope of the invention, the following claims are made.

I claim:

1. A tomographic imaging system comprising:
   (a) a detector providing a plurality of polar values related to physical characteristics of an imaged object associated with corresponding polar volume elements arranged in concentric rings;
   (b) an image processor receiving Cartesian values associated with Cartesian volume elements arranged in rectilinear rows;
   (c) an electronic computer executing a stored program to receive the polar values from the detector and provide Cartesian values to the image processor by:
      (i) identifying the Cartesian volume elements overlapping a current polar volume element in a predetermined mapping of polar volume elements to Cartesian volume elements;
      (ii) for a current identified Cartesian volume element, truncating the current polar volume element to the dimensions of the current identified Cartesian volume element to produce a truncated polar volume element;
      (iii) calculating the area of the truncated polar volume element to produce a weight value identified to both the current identified Cartesian volume element and the current polar volume element, and;
      (iv) repeating steps (ii) and (iii) for each identified Cartesian volume element;
      (iv) repeating steps (i)–(iv) for each polar volume element; and
      (v) determining Cartesian values for the Cartesian volume elements to the image processor, where each Cartesian value is the sum, over all weight values associated with the Cartesian volume element, of the product of the weight value times the polar value of the polar volume element identified with the weight value.

2. The tomographic imaging system recited in claim 1 wherein the detector is an x-ray detector and Fourier transform circuit and the polar values are Fourier transformed x-ray attenuation data acquired by a computed tomography system.

3. The tomographic imaging system recited in claim 1 wherein the detector is an NMR acquisition circuit of an MRI machine and the polar values are sampled NMR signals acquired by the MRI system.

4. The tomographic imaging system recited in claim 1 wherein the detector includes an image reconstruction circuit and wherein the polar volume elements are pixels in an image and wherein the polar values denote a brightness of the pixels.

5. The tomographic imaging system recited in claim 1 wherein the image processor includes a display device and the Cartesian volume elements are pixels in an image and wherein the Cartesian values denote a brightness of the pixels.

6. The tomographic imaging system recited in claim 1 wherein an origin defining the polar volume elements and an origin of axes defining the Cartesian volume elements are the same and where the predetermined mapping ensures that boundaries between polar volume elements lie along the axes.

7. The tomographic imaging system recited in claim 1 wherein step (ii) evaluates a series of segments defining the current polar volume element and calculates intersections between those segments and similar segments defining the identified Cartesian volume element to create a new series of segments defining the truncated polar volume element.

8. The tomographic imaging system recited in claim 1 wherein the polar volume elements are also arranged in sectors.

9. The tomographic imaging system recited in claim 1 wherein the Cartesian volume elements are also arranged in rectilinear columns perpendicular to the rows.

10. A method of producing tomographic images comprising the steps of:
   (a) acquiring a plurality of polar values related to physical characteristics of corresponding polar volume elements within an imaged object, the polar volume elements arranged in concentric rings;
   (c) employing an electronic computer receiving the polar values from the detector and executing a stored program to produce Cartesian values associated with Cartesian volume elements arranged in rectilinear rows according to the following steps:
      (i) identifying the Cartesian volume elements overlapping a current polar volume element in a desired mapping of polar volume elements to Cartesian volume elements;
      (ii) for each identified Cartesian volume element, truncating the current polar volume element to the dimensions of the Cartesian volume element to produce a truncated polar volume element;
      (iii) calculating the area of the truncated polar volume element to produce a weight value identified to both the Cartesian volume elements and the current polar volume element, and;

(iv) repeating steps (i)–(iii) for each polar volume element; and (v) providing Cartesian values for Cartesian volume elements to the image processor, where each Cartesian value is the sum, over all weight values associated with the Cartesian volume element, of the product of the weight value times the polar value of the polar volume element identified with the weight value.

11. The method as recited in claim 10 wherein the polar values acquired by a magnetic resonance imaging system and are sampled nuclear magnetic resonance signals.

12. The method as recited in claim 10 wherein step (ii) evaluates a series of segments defining the current polar volume element and calculates intersections between those segments and similar segments defining the identified Cartesian volume element to create a new series of segments defining the truncated polar volume element.

13. The method as recited in claim 10 wherein the polar volume elements are also arranged in sectors.

14. The method as recited in claim 10 wherein the Cartesian volume elements are also arranged in rectilinear columns perpendicular to the rows.

* * * * *

UNITED STATES PATENT AND TRADEMARK OFFICE
CERTIFICATE OF CORRECTION

PATENT NO. : 5,483,567
DATED : January 9, 1996
INVENTOR(S) : Stuart J. Swerdloff It is certified that error appears in the above-identified patent and that said Letters Patent is hereby corrected as shown below:

Col. 1, line 58          "delta" should be --data--.

Col. 7, line 54          "vertex Θα " should be --vertex 73a--.

Signed and Sealed this

Eleventh Day of June, 1996

Attest:

BRUCE LEHMAN

*Attesting Officer*          *Commissioner of Patents and Trademarks*